United States Patent [19]

Dyke

[11] Patent Number: 4,795,850
[45] Date of Patent: Jan. 3, 1989

[54] PROCESS FOR THE PRODUCTION OF A SYNTHESIS GAS CONVERSION CATALYST

[75] Inventor: Andrew F. Dyke, Cheam, England

[73] Assignee: The British Petroleum Company p.l.c., London, England

[21] Appl. No.: 124,919

[22] Filed: Nov. 24, 1987

Related U.S. Application Data

[62] Division of Ser. No. 888,797, Jul. 23, 1986, Pat. No. 4,740,492.

[30] Foreign Application Priority Data

Jul. 31, 1985 [GB] United Kingdom ............... 85/19321

[51] Int. Cl.$^4$ ................................................ C07C 1/04
[52] U.S. Cl. ...................................... 585/500; 585/700; 585/733; 585/900; 585/534; 585/600
[58] Field of Search ............... 502/302, 326; 585/500, 585/943, 700, 661, 654, 418, 900, 733, 534, 600, 603, 534

[56] References Cited

U.S. PATENT DOCUMENTS

| | | | |
|---|---|---|---|
| 4,172,849 | 10/1979 | Drake | 502/304 X |
| 4,634,800 | 1/1987 | Withers | 585/500 |
| 4,670,619 | 6/1987 | Withers | 585/500 |

FOREIGN PATENT DOCUMENTS

| | | | |
|---|---|---|---|
| 5018380 | 2/1950 | Japan | 502/304 |
| 56-81392 | 7/1981 | Japan | 502/304 |
| 2119277 | 10/1983 | United Kingdom . | |

*Primary Examiner*—William R. Dixon, Jr.
*Assistant Examiner*—James M. Hunter, Jr.
*Attorney, Agent, or Firm*—Brooks Haidt Haffner & Delahunty

[57] ABSTRACT

A composition for use after reductive activation as a catalyst in the conversion of synthesis gas to hydrocarbons of carbon number greater than one, which composition before reductive activation has the formula:

$$Ru_a.A_b.XO_x \qquad (I)$$

wherein
A is an alkali metal,
X is a rare earth metal,
a is greater than zero and up to 5% w/w, based on the total weight of the composition,
b is in the range from zero to 5% w/w, based on the total weight of the composition,
x is a number such that the valence requirements of the other elements for oxygen is satisfied, and subject to the requirements of x, X constitutes the remainder of the composition, is produced by the steps of:

(A) bringing together at a temperature below 50° C. a rare earth metal oxide, a solution of a soluble salt of ruthenium and a precipitant comprising a carbonate and/or a bicarbonate and/or a hydroxide of an alkali metal or ammonium under conditions whereby ruthenium is precipitated in the form of a heat decomposable compound, (B) recovering the mixture of the rare earth metal oxide and the precipitated ruthenium compound obtained in step A, (C) thermally decomposing thermally decomposable compounds comprised in the mixture recovered in step (B).

5 Claims, No Drawings

PROCESS FOR THE PRODUCTION OF A SYNTHESIS GAS CONVERSION CATALYST

This application is a division of application Ser. No. 888,797 filed July 23, 1986 now U.S. Pat. No. 4,740,492 issued Apr. 26, 1988.

The present invention relates to a catalyst for use in the conversion of gaseous mixtures comprising principally carbon monoxide and hydrogen (synthesis gas) to hydrocarbons of carbon number greater than one, in particular to aliphatic hydrocarbons in the gasoline boiling range, to a process for producing the catalyst and to a process utilising the catalyst in the conversion of synthesis gas to the aforesaid hydrocarbons.

The conversion of synthesis gas to hydrocarbons by the Fishcer-Tropsch process has been known for many years but the process has only achieved commercial significance in countries such as South Africa where unique economic factors prevail. The growing importance of alternative energy sources such as coal and natural gas has focussed renewed interest in the Fischer-Tropsch process as one of the more attractive direct and environmentally acceptable routes to high quality transportation fuels.

Of the Group VIII metals, ruthenium has long been known to be one of the most active catalysts in the conversion of synthesis gas, the product, at moderate pressures and above, being high molecular weight paraffin waxes and, at low pressures, principally methane. Several recent patent publications, for example U.S. Pat. Nos. 4,042,614; 4,171,320; 4,206,134; 4,413,064 and 4,410,637 and GB-A-2,119,277, describe and claim the formation of different products from synthesis gas using catalysts containing ruthenium as an active component.

U.S. Pat. No. 4,042,614 describes a process for the selective synthesis of olefins from $C_2$ to $C_{10}$ chain length inclusive from synthesis gas using as catalyst ruthenium on a titanium-containing oxide support, wherein said titanium-containing oxide support is selected from the group consisting of $TiO_2$, $ZrTiO_4$, $TiO_2$-carbon, $TiO_2$-$Al_2O_3$, $TiO_2$-$SiO_2$, alkaline earth titanates, rare earth titanates and mixtures thereof.

U.S. Pat. No. 4,171,320 describes a process for the synthesis of olefins of from $C_2$ to $C_5$ chain length inclusive from synthesis gas using as catalyst ruthenium on a support selected from the group consisting of $V_2O_3$, $Nb_2O_5$, $Ta_2O_5$, $Al_2O_3$-$V_2O_3$, $Al_2O_3$-$Nb_2O_5$, $Al_2O_3$-$Ta_2O_5$, $SiO_2$-$V_2O_3$, $SiO_2$-$Nb_2O_5$, $SiO_2$-$Ta_2O_5$, $V_2O_3$-carbon, $Nb_2O_5$-carbon, $Ta_2O_5$-carbon, alkaline earth-group VB oxides, alkali metal-Group VB oxides, Group IVB-Group VB oxides and mixtures thereof.

U.S. Pat. No. 4,206,134 describes a process for the enhanced synthesis of $C_2$–$C_4$ olefins with reduced production of methane from synthesis gas using as catalyst ruthenium on a manganese-containing oxide support, wherein said manganese-containing oxide support is selected from the group consisting of MnO, $Al_2O_3$-MnO, MnO-carbon, Group IVB-manganese oxide, Group VB-manganese oxides, rare earth-manganese oxides and mixtures thereof.

U.S. Pat. No. 4,413,064 describes a process for the conversion of synthesis gas to a product high in straight chain paraffins in the diesel fuel boiling range from synthesis gas utilising a catalyst consisting essentially of cobalt, thoria or lanthana and ruthenium on an alumina support wherein said alumina is gamma-alumina, eta-alumina or a mixture thereof, said catalyst being prepared by contacting finely divided alumina with (A) an aqueous impregnation solution of a cobalt salt, and (B) a non-aqueous, organic impregnation solution of a ruthenium salt and a salt of thorium or lanthanum.

U.S. Pat. No. 4,410,637 describes a process for the preparation of a hydrocarbon mixture consisting substantially of $C_5$–$C_{12}$ hydrocarbons from synthesis gas using a catalyst containing one or more of iron, nickel, cobalt, chromium and/or ruthenium and, as a carrier, magadite, a laminar crystalline silicate compound capable of absorbing metal ions or metal salts by intercalation.

Finally, GB-A-2,119,277 describes a catalyst for the selective synthesis of olefins from a mixture of hydrogen and carbon monoxide or hydrogen and carbon dioxide comprising a ruthenium carbonyl compound deposited on a ceric oxide-containing support. In Example 3 there is disclosed a catalyst prepared by impregnating ceric oxide with an aqueous solution of $RuCl_3.3H_2O$ (ruthenium content 0.62% w/w). Comparison of the ruthenium carbonyl catalyst with the ruthenium-impregnated catalyst for the conversion of synthesis gas demonstrates that the former catalyst produces considerably less methane and significantly more olefins than the latter catalyst.

We have now found that ruthenium-containing catalysts produced by precipitating the ruthenium component can substantially overcome the disadvantages in terms of high methane yield and low selectivity to olefins reported for the prior art ruthenium impregnated catalysts.

Accordingly the present invention provides a process for the production of a composition for use after reductive activation as a catalyst in the conversion of synthesis gas to hydrocarbons of carbon number greater than one, which composition before reductive activation has the formula:

$$Ru_a.A_b.XO_x \qquad (I)$$

wherein

A is an alkali metal,

X is a rare earth metal, a is greater than zero and up to 5% w/w, based on the total weight of the composition, b is in the range from zero to 5% w/w, based on the total weight of the composition, x is a number such that the valence requirements of the other elements for oxygen is satisfied, and subject to the requirements of x, X constitutes the remainder of the composition, which process comprises the steps of:

(A) bringing together at a temperature below 50° C. a rare earth metal oxide, a solution of a soluble salt of ruthenium and a precipitant comprising a carbonate and/or a bicarbonate and/or a hydroxide of an alkali metal or ammonium under conditions whereby ruthenium is precipitated in the form of a heat decomposable compound, (B) recovering the mixture of the rare earth metal oxide and the precipitated ruthenium compound obtained in step A, (C) thermally decomposing thermally decomposable compounds comprised in the mixture recovered in step (B).

For the purpose of the present invention rare earth metals are defined as metals having atomic numbers of from 57 to 71 inclusive. A preferred rare earth metal oxide is ceria ($CeO_2$) which may be in a substantially pure form or may be in the form of a mixture with other rare earth metal oxides, in which form it may be obtained commercially.

In the composition of formula (I) A is an alkali metal, which largely for reasons of availability and cost, is preferably either sodium or potassium. X as mentioned hereinbefore is preferably cerium. Preferably the amount (b) of alkali metal is less than 2% w/w, even more preferably less than 1% w/w. a in the formula (I) is preferably less than 1% w/w.

As regards step (A) of the process, the rare earth metal oxide may suitably be brought together with an aqueous solution of a water soluble salt of ruthenium, in which solution the rare earth metal oxide is substantially insoluble. Suitably an aqueous solution of the precipitant may be added to an aqueous solution of the ruthenium salt containing also the rare earth metal oxide, though other variants of the order of addition will be readily apparent to those skilled in the art and may be used if desired. Whilst any soluble salt of ruthenium may be employed, it will usually be found convenient to use ruthenium in the form of the chloride because this is a commercially available form.

The precipitant may be a carbonate and/or a bicarbonate and/or a hydroxide of an alkali metal, which is preferably either sodium or potassium. Instead of using a pre-formed carbonate or bicarbonate it is possible to use the precursors of these salts, for example a water soluble salt and carbon dioxide. In any event, b in the aforesaid formula (I) will have a value greater than zero, which value may be adjusted if desired by washing or addition of further alkali metal compound. Alternatively, ammonium carbonate and/or bicarbonate and/or hydroxide may be employed as the precipitant, in which case the value of b in the catalyst as initially produced will be zero, though this value may subsequently be adjusted if desired by addition of alkali metal.

The precipitation is preferably carried out at a temperature below 30° C. It will usually be found convenient to operate at room temperature, for example 15° to 25° C. Catalysts produced at low temperatures are generally more active than similar catalysts wherein the ruthenium is precipitated at high, for example, 80°-90° C., temperatures.

Addition of the precipitant to the solution of the ruthenium salt causes the initially low pH of the mixture to rise. It is desirable in the preparation of catalysts according to the invention that the final pH of the mixture is greater than 6, preferably in the range from 6 to 10, even more preferably in the range from 8 to 10. The precipitant may be added until a pH in the aforesaid range is achieved, whereupon the addition of further precipitant may be discontinued, thereby arresting the rise in the pH. In order to improve the homogeneity of the catalyst it is preferred to agitate the mixture during precipitation, suitably by mechanical stirring. After precipitation, it is preferred to maintain the mixture at a temperaure close to boiling for a period of at least 15 minutes, preferably whilst stirring, for the purpose of completing the precipitation.

The amounts of the reagents employed should be such as to satisfy the stoichiometric relationships in the formula (I).

In step (B) of the process of the invention the precipitate obtained in step (A) is recovered. This may suitably be accomplished by filtration but other methods for separating solids from liquids, for example centrifugation, may be employed. After recovery it is preferred to wash the precipitate, suitably with water, so as to remove unwanted residual soluble matter. It is also preferred to dry the precipitate, suitably at an elevated temperature below 150° C., for example about 120° C.

In step (C) of the process thermally decomposable compounds comprised in the mixture obtained in step (B) are thermally decomposed. This may suitably be achieved by heating the mixture, suitably in a non-reducing atmosphere, for example a stream of inert gas, such as nitrogen, or an oxygen-containing gas, such as air, at a temperature suitably in the range from 250° to 600° C.

Before use as a catalyst in the production of hydrocarbons from synthesis gas it is necessary for the composition of formula (I) to be reductively activated. Reductive activation may be accomplished by contacting the composition at elevated temperature with a reducing gas, for example hydrogen which may be diluted with an inert gas such as nitrogen. Typically, the conditions employed may suitably be a pressure in the range from 1 to 100 bar and a temperature in the range from 150° to 300° C., suitably for a period of up to 24 hours or longer. Whilst it is preferred to effect the reductive activation step as a discrete step prior to use as a catalyst for the conversion of synthesis gas, it may be incorporated into the synthesis gas conversion process and effected 'in situ'.

It will be appreciated by those skilled in the art that under certain circumstances the thermal decomposition step [step B] and the reductive activation may be accomplished in one and the same operation, therby simplifying the process.

The present invention also provides a process for the production of hydrocarbons having a carbon number greater than one from synthesis gas which process comprises contacting synthesis gas with the reductively activated composition of formula (I) at a temperature in the range from 190° to 400° C. and a pressure in the range from 0 to 100 bar.

As is well known in the art synthesis gas principally comprises carbon monoxide and hydrogen and possibly also minor amounts of carbon dioxide, nitrogen and other inert gases depending upon its origin and degree of purity. Methods for preparing synthesis gas are established in the art and usually involve the partial oxidation of a carbonaceous substance, e.g. coal. Alternatively, synthesis gas may be prepared, for example by the catalytic steam reforming of methane. For the purpose of the present invention the carbon monoxide to hydrogen ratio may suitably be in the range from 2:1 to 1:6. Whilst the ratio of the carbon monoxide to hydrogen in the synthesis gas produced by the aforesaid processes may differ from these ranges, it may be altered appropriately by the addition of either carbon monoxide or hydrogen, or may be adjusted by the so-called shift reaction well known to those skilled in the art.

The temperature is preferably in the range from 250° to 350° C. and the pressure is preferably in the range from 10 to 50 bar. The GHSV may suitably be in the range from 100 to 5000 $h^{-1}$.

The process may be carried out batchwise or continuously in a fixed bed, fluidised bed or slurry phase reactor.

In a modification of the process for the production of hydrocarbons, there may be combined with the catalyst an inert material, for example silica. It is preferred, however, to combine the catalyst with a zeolite.

The zeolite may be either physically admixed with the composition to form an intimately mixed bed or may be separate therefrom, for example in the form of a split bed, the zeolite forming one portion of the bed and the catalyst another. In the case of a physical admixture, the zeolite may be mixed with the composition either before or after reductive activation. Alternatively, the precipitation (step A) in the process for producing the composition of formula (I) may be performed in the presence of the zeolite, particularly when the precipitant is ammonium carbonate and/or bicarbonate and/or hydroxide.

A suitable zeolite is an MFI-type zeolite, for example ZSM-5 as described in U.S. Pat. No. 3,702,886. It is preferred to use the hydrogen form of the zeolite which may be obtained by acid exchange or by thermal decomposition of the ammonium-exchanged form of the zeolite. Preferably the alkali metal-free composition (b in the formula (I)=0) is modified by combination with the zeolite. Suitably the ratio of the number of parts by volume of catalyst composition to the number of parts by volume of the zeolite may be in the range from 5:1 to 1:5, preferably about 2:1. Combination with a zeolite can improve the selectivity to gasoline range paraffinic hydrocarbons.

DETAILED DESCRIPTION OF INVENTION

The invention will now be further illustrated by the following Examples. In all the synthesis gas conversion reactions there was employed the same slurry phase reactor using fine particles of the catalyst suspended in a hydrocarbon wax.

CATALYST PREPARATION

EXAMPLE 1

Catalyst A (0.5% w/w Ru on ceria)

Cerium oxide ($CeO_2$, 60 g; 0.349 mol) was added to a 500 ml solution of ruthenium chloride ($RuCl_3.2H_2O$, 0.72 g; 0.003 mol) and stirred vigorously for one hour. To this a 50 ml solution of sodium carbonate ($Na_2CO_3.10H_2O$, 2.55 g; 0.009 mol) was added at room temperature (about 20° C.) dropwise over 30 minutes. After a further hour the solution was heated to boiling to ensure complete hydrolysis of the ruthenium chloride. After holding for 30 minutes a solution of sodium formate (NaHCO, 0.95 g; 0.018 mol) in 50 mls water was added over 30 minutes to the boiling solution. After a further hour the catalyst slurry was allowed to cool, was filtered and extremely thoroughly washed with water. After drying in an oven for 16 hours at 125° C., the catalyst was activated under a steady stream of hydrogen for 16 hours at 270° C. before testing.

EXAMPLE 2

Catalyst B (0.5% w/w Ru on ceria)

Cerium oxide ($CeO_2$, 40 g; 0.233 mol) was added to a 500 ml soluton of ruthenium chloride ($RuCl_3.2H_2O$, 0.48 g; 0.002 mol) and vigorously stirred for 30 minutes. To this ammonium carbonate ($NH_4HCO_3.NH_2COOHN_4$, 1.5 g: 0.010 mol) dissolved in 50 mls water was added at room temperature (about 20° C.) dropwise over a further 30 minutes. The slurry was then cold stirred for one hour, before heating to boiling for a further one hour to ensure complete ruthenium chloride hydrolysis. The mixture was then allowed to cool, filtered and was thoroughly washed before drying in an oven at 125° C. for 16 hours.

This catalyst was activated under hydrogen as in Example 1.

EXAMPLE 3

Catalyst C (0.5% w/w Ru on ceria)

Cerium oxide ($CeO_2$, 40 g; 0.233 mol) was placed in an evaporating basin heated on a steam bath. Ruthenium chloride ($RuCl_3.2H_2O$, 0.48 g; 0.002 mol) dissolved in 50 mls water was slowly added, stirring the mixture continuously as the water dried off. After complete addition the catalyst cake was dried at 125° C. for 8 hours in an oven.

The catalyst was activated as in Example 1.

EXAMPLE 4

Catalyst D (0.5%, w/w Ru on ceria)

Cerium oxide ($CeO_2$, 40 g; 0.233 mol) was added to a 500 ml solution of ruthenium chloride ($RuCl_3.2H_2O$, 0.48 g; 0.002 mol) and stirred for 30 minutes. The mixture was then heated to boiling. Ammonium carbonate ($NH_4HCO_3.NH_2COONH_4$, 1.5 g; 0.010 mol) dissolved in 50 ml water was added dropwise over a further 30 minutes. After 1 hour of slurrying the mixture was allowed to cool, was filtered and thoroughly washed. The catalyst was then dried for 16 hours at 125° C., before activation in the same way as Example 1.

CATALYST TESTING

EXAMPLE 5

The Catalyst (A) of Example 1 was tested for the conversion of synthesis gas to hydrocarbons in a slurry phase reactor under the following conditions:
$CO:H_2$ (molar ratio)=1:2
Pressure=20 bars
Temperature=290° C.
GHSV (based on wax)=268 $h^{-1}$
The results are given in the Table.

EXAMPLE 6

Example 5 was repeated except that the Catalyst (B) of Example 2 was used in place of Catalyst (A).

EXAMPLE 7

Example 5 was repeated except that the Catalyst (C) of Example 3 was used in place of Catalyst A.

EXAMPLE 8

Example 5 was repeated except that the Catalyst (D) of Example 4 was used in place of Catalyst (A).

The results of Examples 6 to 8 are given in the Table.

TABLE

| | | | Molar Selectivity (%) | | |
|---|---|---|---|---|---|
| Example | Catalyst | Conversion | $CO_2$ | $CH_4$ | $C_5^+$ hydrocarbons |
| 5 | A | 30 | 2.7 | 14.7 | 46.5 |
| 6 | B | 36 | 2.2 | 13.5 | 46.6 |
| 7 | C | 36 | 0.85 | 25.6 | 38.8 |
| 8 | D | 8 | 2.7 | 17.2 | 38.8 |

We claim:
1. A process for the production of hydrocarbons having a carbon number greater than one from synthesis gas which process comprises contacting synthesis gas with a catalyst at a temperature in the range from 190° to 400° C. and a pressure in the range from 0 to 100 bar, said catalyst comprising a reductively activated composition, which composition before reductive activation has the formula:

$$Ru_a A_b XO_x \qquad (I)$$

wherein

A is an alkali metal,

X is a rare earth metal, a is greater than zero and up to 5% w/w, based on the total weight of the composition, b is in the range from zero to 5% w/w based on the total weight of the composition, x is a number such that the valence requirements of the other elements for oxygen is satisfied, and subject to the requirements of x, X constitutes the remainder of the composition.

2. A process according to claim 1 wherein the temperaure is in the range from 250° to 350° C. and the pressure is in the range from 10 to 50 bar.

3. A process according to claim 1 wherein the catalyst is in a slurry phase.

4. A process according to claim 1 wherein the reductively activated composition of formula (I) is combined with a zeolite.

5. A process according to claim 4 wherein the zeolite is ZSM-5 in the hydrogen form.